United States Patent
Bleiner et al.

(10) Patent No.: US 10,366,863 B2
(45) Date of Patent: Jul. 30, 2019

(54) DETECTOR SUPPLEMENT DEVICE FOR SPECTROSCOPY SETUP

(71) Applicant: EMPA Eidgenössische Materialprüfungs-und Forschungsanstalt, Dübendorf (CH)

(72) Inventors: Davide Bleiner, Zürich (CH); Yunieski Arbelo-Pena, Bern (CH)

(73) Assignee: EMPA EIDGENÖSSISCHE MATERIALPRÜFUNGS-UND FORSCHUNGSANSTALT, Dübendorf (CH)

( * ) Notice: Subject to any disclaimer, the term of this patent is extended or adjusted under 35 U.S.C. 154(b) by 0 days.

(21) Appl. No.: 15/779,235

(22) PCT Filed: Nov. 25, 2016

(86) PCT No.: PCT/EP2016/078771
§ 371 (c)(1),
(2) Date: May 25, 2018

(87) PCT Pub. No.: WO2017/089517
PCT Pub. Date: Jun. 1, 2017

(65) Prior Publication Data
US 2018/0350556 A1    Dec. 6, 2018

(30) Foreign Application Priority Data
Nov. 26, 2015 (EP) .................................... 15196565

(51) Int. Cl.
*H01J 37/285* (2006.01)
*H01J 37/244* (2006.01)
(Continued)

(52) U.S. Cl.
CPC .......... *H01J 37/285* (2013.01); *G01N 23/227* (2013.01); *G01R 15/181* (2013.01); *H01J 37/244* (2013.01); *H01J 2237/2855* (2013.01)

(58) Field of Classification Search
CPC ............ G01N 23/227; G01N 23/2273; G01N 23/2276; H01J 2237/2855; H01J 37/244; H01J 37/285
See application file for complete search history.

(56) References Cited

U.S. PATENT DOCUMENTS

| | | |
|---|---|---|
| 3,835,330 A | 9/1974 | Baker et al. |
| 2002/0134757 A1 | 9/2002 | Nishizumi et al. |

(Continued)

FOREIGN PATENT DOCUMENTS

KR    20090107841 A    10/2009

OTHER PUBLICATIONS

International Search Report dated Feb. 3, 2017 for PCT/EP2016/078771 filed Nov. 25, 2016.
(Continued)

*Primary Examiner* — Nicole M Ippolito
*Assistant Examiner* — Sean M Luck
(74) *Attorney, Agent, or Firm* — Paul D. Bianco; Gary S. Winer; Fleit Gibbons Gutman Bongini & Bianco PL

(57) ABSTRACT

A detector supplement device for integration in a spectroscopy setup with the spectroscopy setup including a vacuum chamber, a light source, a sample irradiating a reflected photon beam and a charged particle beam in the same direction of propagation into a radiation detector which is able to detect ultrafast electric currents originating from charged particles. The detector supplement device includes a Rogowski coil placeable inside the vacuum chamber between the sample and radiation detector. The charged particle beam is guided through the hollow core of the
(Continued)

Rogowski coil allowing synchronized measurements of electrical currents due to the charged particle beam correlated to the reflected photon beam, while irradiation of the reflected photon beam and the charged particle beam takes place in the same direction of propagation.

10 Claims, 4 Drawing Sheets

(51) Int. Cl.
     *G01N 23/227*     (2018.01)
     *G01R 15/18*      (2006.01)

(56) References Cited

U.S. PATENT DOCUMENTS

2008/0036448 A1     2/2008   Kovach et al.
2018/0350556 A1*  12/2018  Bleiner ............... G01N 23/227

OTHER PUBLICATIONS

Written Opinion for PCT/EP2016/078771 filed Nov. 25, 2016.
Woodruff Scientific: "Magnetic probes". Internet Citation, Oct. 15, 2015 (Oct. 15, 2015). pp. 1-4. XP008180347. Retrieved from the Internet: URL: http://web.archive.org/web/20151015020322/http://www.woodruffscientific.com/magnetic [retrieved on May 23, 2016].
International Preliminary Report on Patentability with Written Opinion dated May 29, 2018 for PCT/EP2016/078771 filed Nov. 25, 2016.

* cited by examiner

DETECTOR SUPPLEMENT DEVICE FOR SPECTROSCOPY SETUP

TECHNICAL FIELD

The present invention describes a detector supplement device for integration in a spectroscopy setup, wherein the spectroscopy setup comprises a vacuum chamber, a light source, a sample irradiating a reflected photon beam and a charged particle beam in the same direction of propagation into a radiation detector, use of a Rogowski coil in a vacuum chamber of a spectroscopy setup, wherein the spectroscopy setup comprises a sample irradiating a reflected photon beam and a charged particle beam in the same direction of propagation into a radiation detector, as well as a manufacturing method for upgrading a spectroscopy setup, wherein the spectroscopy setup comprises a vacuum chamber, a light source, a sample irradiating a reflected photon beam and a charged particle beam in the same direction of propagation into a radiation detector.

STATE OF THE ART

State-of-art detectors used in photoemission spectrometry are based on different architectures of electron multipliers such as Microchannel plates (MCP) or Single Channel electron multipliers (CEM). Ultrafast designs based in the MCP technology, can provide electron multiplication values of around $10^6$ and response times as low as 200 ps. In the same way, the CEMs allows typical gains of $10^8$ and output pulse widths from 10 ns to 20 ns.

The MCP configuration has been used in time-resolved photoelectron spectroscopy, driven with soft x-ray radiation to analyze molecular bonding. However, limitations regarding saturation due to high number of electrons hitting the MCP, in a time shorter than its response time were reported.

The electron multipliers CEM have been similarly implemented in time of flight mass spectrometry (TOFMS). In this technique, packets of ions are periodically pulsed into the entrance of a field-free drift chamber to be detected. In practice, the duty cycle is limited by modulation i.e. pulsed sampling to avoid ion bunch overlapping. The duration between pulses has to be set longer than the flight time of the heaviest ion in the bunch.

However, as a first drawback, this restricts the possibility of using high repetition rate sources for ionization of the sample to enhance the duty cycle. A further drawback of the discussed detectors is that they stop the incident beam to be measured e.g. electrons/ions or photons. This restricts the possibility of performing correlated measurements of photon-photoelectron signals in the same direction of propagation. Such measurements are attractive for photoemission spectrometry. For instance, after ionization of the sample, photoemission and relaxation via Auger or X-ray can take place. If the X-rays are emitted in the same direction of propagation than the photoelectrons are detected with the electron multiplier, the output spectrum could be affected.

DESCRIPTION OF THE INVENTION

The object of the present invention is to create a possibility for spectroscopy setups combining measurements of photons and charged particles in the same direction of propagation, leading to synchronized measurements of photons and charged particles and detection of ultrafast electric currents originating from charged particles.

Ultrafast photocurrents are not handled with state-of-art detectors, because of low-pass cut-off frequencies, low duty cycle, neutralization of positive and negative charges, and impossibility of coincidence measurement of photon and electrons/ions.

The problem is solved by introducing a detector supplement device for commercially available detectors, which can be easily integrated in a photoemission spectroscopy or time of flight mass spectrometry setup.

The detector supplement as disclosed in the following is based on a toroidal coil through which the electrons/ions-currents to be measured are passed, thus inducing a current upon increase of a field.

By using the detector supplement device as an upgrade of known spectroscopy setups, the detection of correlated photons and photoelectrons in the same direction of propagation is possible.

Also existing spectroscopy setups can be upgraded with the here described detector supplement device.

BRIEF DESCRIPTION OF THE DRAWINGS

A preferred exemplary embodiment of the subject matter of the invention is described below in conjunction with the attached drawings.

FIG. 2a shows a schematic view of a Rogowski coil on which the detector supplement device is based, while

DESCRIPTION

In spectroscopy setups 0, where photons and correlated charged particles as for example electrons are propagating in the same direction, a detector supplement 4 can be used for additionally synchronized measuring current signals, while radiating a sample 3 is carried out.

Figure 1:
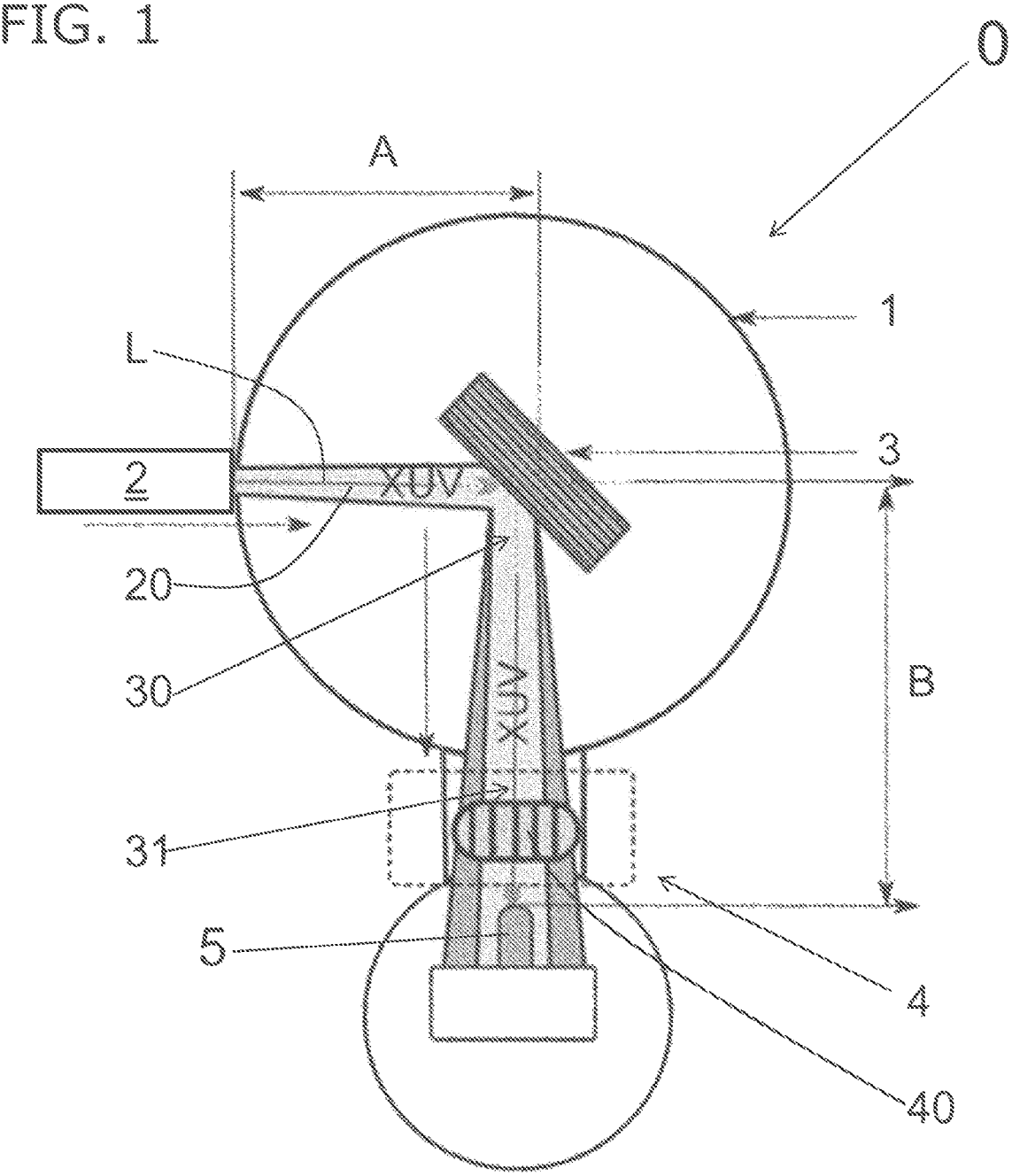
FIG. 1 shows a schematic of an experimental set up used for the detection of correlated photons and photoelectrons in the same direction of propagation. The XUV radiation emitted from the XUV-source is reflected from the multilayer and detected with the AXUV-photodiode. The correlated photoemission is detected with a detector supplement device.

As an example a photoemission spectroscopy setup 0 is depicted in FIG. 1, comprising a light source 2, here a plasma source or gas-discharge XUV-source 2 is used irradiating into a vacuum chamber 1 onto a sample 3 in form of a multilayer 3 within a distance A. The radiation beam 20 or incident photon beam 20 is reflected at the multilayer 3, forming a reflected photon beam 30. Also photoelectrons 31 (charged particle beam) are emitted from the sample 3 correlated to the photons, while the reflected photon beam 30 and the photoelectrons 31 are propagating in the same direction.

Before the charged particles in form of photoelectrons 31 reach the radiation detector 5, they are guided through a detector supplement device 4, comprising a Rogowski coil 40. The detector supplement device 4 is based on a hollow-cored toroidal coil, known as Rogowski coil 40 with characteristic form and windings, through which the charged particles-(electrons/ions)-currents to be measured are passed. The Rogowski coil 40 has therefore to be placed in the vacuum chamber 1 of the spectroscopy setup 0, that the charged particle beam 31 can pass the hollow core in a centric way. Of course also the photons can pass the hollow-cored toroidal coil. Beside the Rogowski coil 40, a terminal resistor R, an optional toroid support, necessary electrical connection and an electrical circuit, for example an integrator circuit forming parts of the detector supplement device 4.

The rate of change of the input current, diin(t)/dt, induces a current in the detector supplement device 4 respectively in the Rogowski coil 40, measured as a voltage, Uout(t), across the terminal resistor R.

As known from a Rogowski coil 40, the used Rogowski coil 40 comprises a helical coil of wire, with windings surrounding a toroid support S, while the inner core of the Rogowski coil 40 is empty, allowing the passing of a charged particle beam 31 through the center. To prevent the influence of ambient fields, the detector supplement device 4 is designed with two wire-loops in opposite windings. This allows the cancellation of electromagnetic fields outside the detector supplement device 4. The primary loop is made-up of turns of the coil, and the second loop can be formed by returning the wire through the center of the winding. The lead from the one end is fed back through the centre of the toroid support S to the other end, so that both terminals are at the same end of the Rogowski coil 40.

In a preferred embodiment the toroid support S should be non-magnetic. A thermoplastic was used for the toroid support S.

For mechanical stability the toroid support S is used, in particular formed as a tube. Suitable materials for the toroid support S are thermoplastics or for example rubber. Depending on the vacuum properties of the spectroscopy method for which the detector supplement device 4 should be used, the material of the toroid support S should be ultrahigh vacuum compatible. For ultrahigh vacuum setups, the assembly of the detector can be carried out without a toroid support S.

The input to output transfer function of the detector supplement device 4 can be determined considering the equivalent circuit with terminal resistance, R. In practice, the response of the detector supplement device 4 respectively the Rogowski coil 40 used, is ruled by the selection of the geometry of the core inner diameter a, external diameter or width b and height or thickness h, terminal resistor R and the number of turns or windings N.

The detector supplement device 4 overcomes the restrictions known for the state-of-art detectors. A faster response time can be obtained (e.g. one order of magnitude). An attractive advantage for TOFMS is in the possibility of achieving 100% of duty cycle when continuous ionization sources are used.

The detector supplement device 4—is not affected by overlapping of ions packets since it measures in Fourier space. On the other hand, correlated measurements of photon/photoelectrons in the same direction of propagation can be realized. This is possible due to the sensitivity only to electron/ion currents and the hollow-cored configuration of the detector supplement device 4.

In practice the output signal of the detector supplement device 4 must be passed through an integrator circuit to obtain the input current wave-form. However, self-integration techniques can be implemented. The achieved output signals of the detector supplement device 4 could be also used for self-triggering the measurement setup.

Figure 2A:
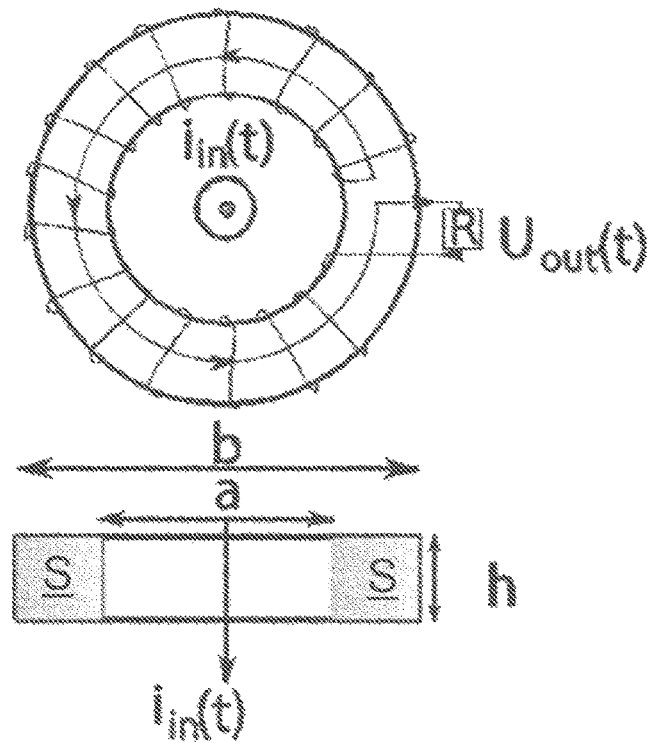
Figure 2B:
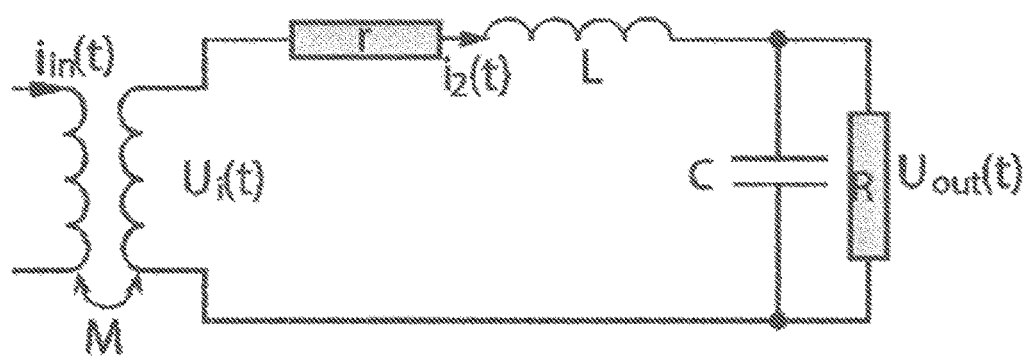
FIG. 2b shows the equivalent circuit of the Rogowski coil.

The input charged particle (electron/ion) currents, $i_{in}(t)$, output voltage, $U_{out}(t)$, terminal resistance, R, and geometric parameters of the Rogowski coil 40 are presented in FIG. 2a, while FIG. 2b shows the equivalent circuit with terminal resistance, R, considered for the obtaining of the input to output transfer function of the detector supplement device 4.

The input to output transfer function of the detector supplement device 4, $H(s)$, as a function of the output voltage, $U_{out}(s)$, the input current, $I_{in}(s)$, the Laplace variable, s, the mutual inductance, M, the capacitance of the windings, C, the self-inductance, L, the resistance of the windings, r and R can be obtained as follows:

$$H(s) = \frac{U_{out}(s)}{I_{in}(s)} = \frac{Ms}{LCs^2 + \left(\frac{L}{R} + rC\right)s + \frac{R+r}{R}} \quad (1)$$

Considering Eq. (1) and imposing L/RrC>>1, the lower ($f_l$) and higher ($f_h$) cut-off frequencies of the detector supplement device 4 can be obtained as follows:

$$f_l = \frac{R+r}{2\pi(L + RrC)} \approx \frac{R}{2\pi L} \quad (2)$$

$$f_h = \frac{L + RrC}{2\pi LRC} \approx \frac{1}{2\pi RC} \quad (3)$$

Consequently, the band width of the detector supplement device 4 can be determined as:

$$\Delta f = f_h - f_l \approx \frac{1}{2\pi}\left(\frac{1}{RC} - \frac{R}{L}\right) \quad (4)$$

As can be appreciated, the band width of the detector supplement device 4 can be enhanced e.g. by decreasing the terminal resistance.

FIG. 1 shows the schematics of the experimental set up used for the synchronized detection of correlated photons and photoelectrons. The XUV radiation 20 emitted from the XUV-source 2 is reflected from the multilayer 3 and detected with the AXUV-photodiode 5.

The correlated photoemission, the current in the Rogowski coil 40, is detected with a Rogowski coil 40 with configuration (a): number of windings N=34, height h=10 mm, width b=30 mm, inner diameter a=15 mm and terminal resistance R=50Ω. The multilayer 3 was located at A=540 mm from the plasma-source 2 and positioned at 46°. The AXUV-photodiode 5 was positioned at B=400 mm from the multilayer 3, perpendicularly to the XUV-source axis L. The gas-discharge XUV-source 2 was based on a system of hollow electrodes directly attached to a capacitor bank and operated with Ar at a pressure of $10^{-2}$ mbar. For the operation of the XUV-source 2 a storage capacity of 960 nF and a working voltage of 2.5 kV were used. The pseudo-spark is self-triggered at gas breakdown voltage.

Figure 3:
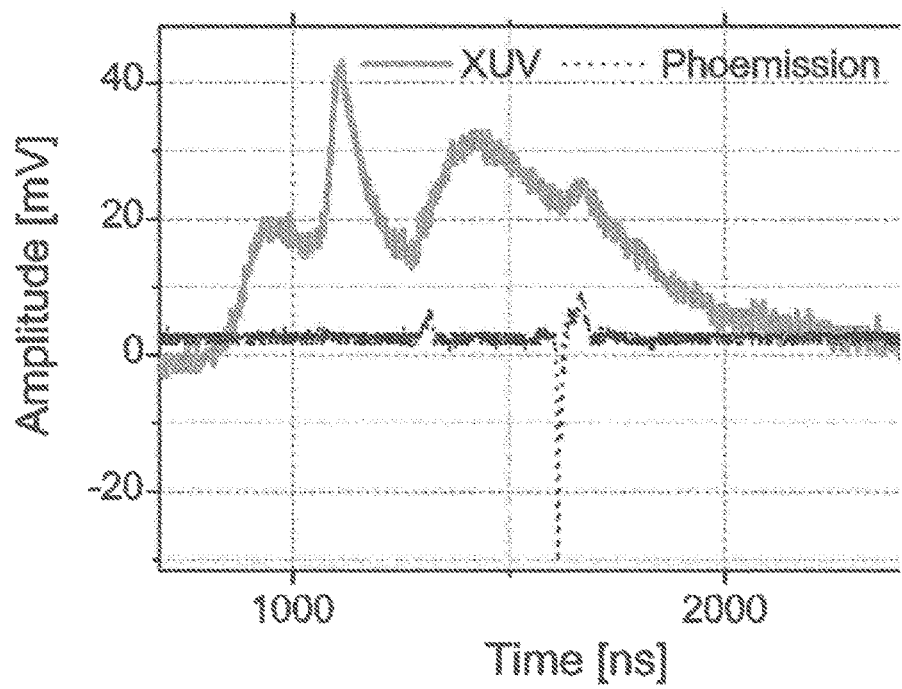
FIG. 3 shows XUV-signal obtained with the AXUV-photodiode and the correlated photoemission acquired with a configuration (a) of the detector supplement device.

FIG. 3 shows the XUV-signal reflected from the multilayer 3 obtained with the AXUV-photodiode 5 and the correlated photoemission acquired with the configuration (a)

of the detector supplement device 4. The measurements were realized in the same direction of propagation as presented in FIG. 1. A current peak in the photoemission signal from the multilayer 3 is clearly visible. This indicates that the detector supplement device 4 provides a differential response of the photo-current.

The frequency-resolved response of the detector supplement device 4 has been simulated and experimentally obtained in order to: a) test the parametric dependence on the detector response and b) to optimize the detector response in the frequency range required to perform photoemission measurements, driven with XUV-pulses generated from a gas-discharge plasma-source 2. FIG. 4 are showing the simulated and experimental frequency-resolved response of four configurations of the detector supplement device 4 respectively the Rogowski coil 40. The lower limit of the range of frequencies required to perform photoemission measurements, driven with XUV-pulses generated from a gas-discharge plasma-source 2 are similarly presented.

Figure 4A:
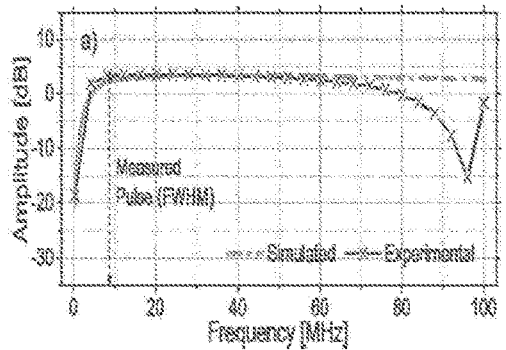
FIGS. 4A-4C are showing experimental and simulated frequency-resolved responses of the detector supplement device with four configurations: (a) N=34, R=50Ω, r=80 mΩ, h=10 mm, b=30 mm and a=15 mm; (b) N=16, R=50Ω, r=40 mΩ, h=10 mm, b=30 mm and a=15 mm; (c) N=34, R=50Ω, r=60 mΩ, h=10 mm, b=30 mm and a=25 mm; (d) N=34, R=50Ω, r=130 mΩ, h=25 mm, b=30 mm and a=15 mm.

FIG. 4(a) shows the experimental and simulated frequency-resolved response of the detector supplement device 4 with the configuration (a), N=34, R=50Ω, r=80 mΩ, h=10 mm, b=30 mm and a=15 mm.

A relative standard deviation of 1.3% is obtained in the range of 4 MHz to 60 MHz. In the same way, a resonance in the response of the detector supplement device 4 in around 96 MHz is observed. These resonances are originated due to self-inductance and capacitance distributed between the windings of the Rogowski coil 40.

Figure 4B:
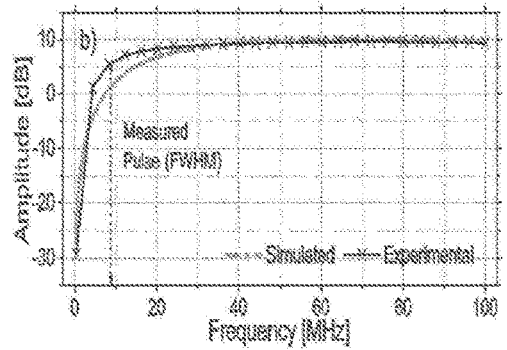

FIG. 4(b) shows the experimental and simulated frequency-resolved response of the detector supplement device 4 reducing number of windings N and keeping the parameters R, h, b and a as in the configuration (a).

A higher lower cut-off frequency and gain are observed as the parameter N is reduced.

Figure 4C:
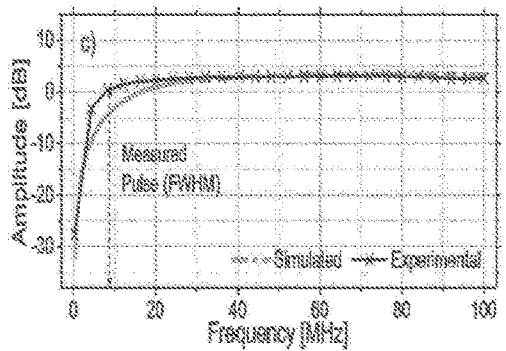

FIG. 4(c) shows the experimental and simulated frequency-resolved response of the detector supplement device 4 increasing inner diameter a and keeping the parameters N, R, h and b as in the configuration (a).

The gain remains the same while the lower cut-off frequency is increased.

Figure 4D:
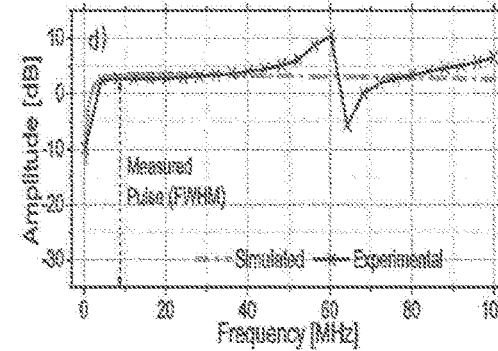

FIG. 4(d) shows the experimental and simulated frequency-resolved response of the detector supplement device 4 increasing height h and keeping the parameters N, R, b and a as in the configuration (a). The same gain is obtained while the lower cut-off frequency is decreased. In a similar way, a resonance is observed in around 60 MHz. For this configuration, a relative standard deviation of 7.4% is obtained in the range of 4 MHz to 60 MHz.

Figure 5:
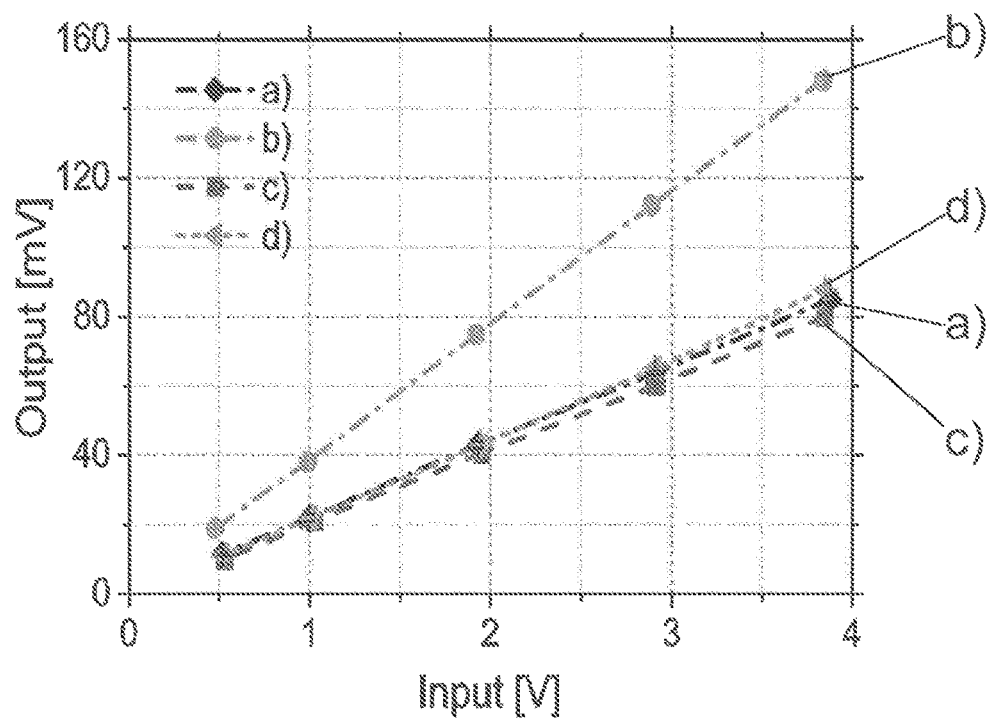
FIG. 5 shows measured linearities of the four above mentioned configurations of the Rogowski coil.

FIG. 5 shows the measured linearity of the detector supplement device 4 with the four configurations presented in FIG. 4. Input waveforms with 30 MHz frequency and peak-peak amplitudes changed in 0.5 V, 1 V, 2 V, 3 V and 4 V were used to measure the output response (peak-peak amplitude) of the detectors.

A linear response is observed for the four configurations of the detector supplement device 4. For the configurations (a), (c) and (d), the same input-output dependence is obtained. On the other hand, a higher response (around factor of 2) is observed for the configuration (b) of the detector supplement device 4. The higher response for this configuration of the detector supplement device 4 is due to the reduction (around factor of 2) in the number of turns.

The detector supplement device 4 can be used for upgrading an existing spectroscopy setup 0. The detector supplement device 4, comprising the Rogowski coil 40 has to be integrated in the vacuum chamber 1 in the path between the sample 3 and the radiation detector 5. The reflected photon beam 30 and the charged particle beam 31 have to be passed through the hollow core of the Rogowski coil 40.

For easy integration of the detector supplement device 4 in a vacuum chamber 1, the Rogowski coil 40 can be integrated in a flange or in a flange-mountable chamber. The terminal resistor R, electrical connection and the electrical circuit can be placed outside the vacuum chamber 1 for simplification.

In another embodiment a multiplicity of detector supplement devices 4 in front of the radiation detector 5 in the pathway between sample 3 and radiation detector 5 are arranged. With a multiplicity of Rogowski coils 40, which are crossed by the charged particle beam 31, an image of current signals of each Rogowski coil 40 can be generated. The arrangement of the Rogowski coils 40 would be in the best way as dense as possible with Rogowski coils 40 as small as possible.

LIST OF REFERENCE NUMERALS 0 spectroscopy setup/Photoemission spectroscopy setup
1 vacuum chamber
2 plasma source/light source
   20 radiation beam/incident photon beam
   L radiation source axis
3 sample/multilayer
   30 reflected photon beam
   31 photoelectrons/e-/charged particle beam
4 detector supplement device
   40 Rogowski coil
   N number of windings
   r resistance of windings
   h height
   b width
   a inner diameter
   S toroid support
   R terminal resistor
   electrical connection
   electrical circuit
5 radiation detector/photodiode/MCP
A distance between vacuum chamber wall and sample
B distance between sample and photodiode

The invention claimed is:

1. A detector supplement device for integration in a spectroscopy setup, wherein the spectroscopy setup comprises a vacuum chamber, a light source, a sample irradiating a reflected photon beam and a charged particle beam in the same direction of propagation into a radiation detector, wherein
   the detector supplement device comprises a Rogowski coil placeable inside the vacuum chamber between the sample and radiation detector, wherein the charged particle beam is guided through the hollow core of the Rogowski coil allowing synchronized measurements of electrical currents due to the charged particle beam correlated to the reflected photon beam, while irradiation of the reflected photon beam and the charged particle beam takes place in the same direction of propagation.

2. The detector supplement device of claim 1, wherein the Rogowski coil is placed in a vacuum flange for easy connection to an existing vacuum chamber of a spectroscopy setup.

3. The detector supplement device of claim 1, wherein a toroid support in form of a polymer, in particular thermoplastic or rubber tube is selected.

4. The detector supplement device of claim 1, wherein a toroid support in form of ultrahigh vacuum compatible material is selected.

5. The detector supplement device of claim 1, wherein a number of windings is selected between 10 to 50 windings.

6. The detector supplement device of claim 1, wherein the dimensions of the Rogwoski coil are
a width of 20 to 40 millimeter,
an inner diameter between 10 and 30 millimeter,
a height between 10 and 40 millimeter.

7. The detector supplement device of claim 1, wherein a multiplicity of Rogowski coils is arranged inside the vacuum chamber between the sample and radiation detector.

8. A manufacturing method for upgrading a spectroscopy setup, wherein the spectroscopy setup comprises a vacuum chamber, a light source, a sample irradiating a reflected photon beam and a charged particle beam in the same direction of propagation into a radiation detector, the method comprising:
adding a detector supplement device, comprising a Rogowski coil to the vacuum chamber of the spectroscopy setup such that the Rogowski coil is placed between the sample and radiation detector and the charged particle beam is guided through the hollow core of the Rogowski coil.

9. The manufacturing method of claim 8, wherein the Rogowski coil is integrated in a flange to be flange-mounted to the vacuum chamber.

10. The manufacturing method of claim 8, wherein a multiplicity of Rogowski coils are arranged inside the vacuum chamber between the sample and radiation detector.

* * * * *